United States Patent

Dönges

[11] 4,371,606
[45] Feb. 1, 1983

[54] 2-(HALOGENOMETHYL-PHENYL)-4-HALOGENO-OXAXOLE DERIVATIVES, A PROCESS FOR THE PREPARATION THEREOF, AND RADIATION-SENSITIVE COMPOSITIONS CONTAINING THESE DERIVATIVES

[75] Inventor: Reinhard Dönges, Bad Soden, Fed. Rep. of Germany

[73] Assignee: Hoechst Aktiengesellschaft, Fed. Rep. of Germany

[21] Appl. No.: 272,049

[22] Filed: Jun. 9, 1981

[30] Foreign Application Priority Data

Jun. 9, 1980 [DE] Fed. Rep. of Germany ....... 3021599

[51] Int. Cl.³ .............................................. G03C 1/72
[52] U.S. Cl. .................................. 430/281; 430/270; 430/286; 430/287; 430/292; 430/294; 430/338; 430/495; 430/541; 430/914; 430/916; 430/920; 430/925; 430/343; 542/400; 542/430; 542/439; 542/454; 542/459; 548/215; 548/219; 548/235

[58] Field of Search ............... 542/400, 430, 439, 454, 542/459; 548/215, 219, 235; 430/270, 281, 286, 287, 292, 294, 338, 343, 495, 541, 914, 916, 920, 925

[56] References Cited

U.S. PATENT DOCUMENTS

| | | | |
|---|---|---|---|
| 3,842,019 | 10/1974 | Kropp | 430/287 |
| 3,879,356 | 4/1975 | Pacifici | 430/287 |
| 3,954,475 | 5/1976 | Bonham et al. | 430/287 |
| 4,189,323 | 2/1980 | Buhr | 430/281 |

*Primary Examiner*—John E. Kittle
*Assistant Examiner*—Robert A. Wax
*Attorney, Agent, or Firm*—James E. Bryan

[57] ABSTRACT

This invention relates to a novel 2-(halogenomethyl-phenyl)-4-halogeno-oxazole derivative; to a radiation-sensitive composition which, as the radiation-sensitive compound, contains a 2-halogenomethyl-phenyl)-4-halogeno-oxazole derivative; and to a process for the preparation of the novel 2-(halogenomethyl-phenyl)-4-halogeno-oxazole derivatives.

11 Claims, No Drawings

2-(HALOGENOMETHYL-PHENYL)-4-HALOGENO-OXAXOLE DERIVATIVES, A PROCESS FOR THE PREPARATION THEREOF, AND RADIATION-SENSITIVE COMPOSITIONS CONTAINING THESE DERIVATIVES

This invention relates to 2-(halogenomethyl-phenyl)-4-halogeno-oxazole derivatives which are substituted in the 5-position of the oxazole ring and, optionally, on the phenyl radical; it also relates to a process for the preparation of these compounds and to radiation-sensitive compositions containing these compounds.

For a considerable length of time, compounds having halogenomethyl groups have played an important role as precursors, intermediates and final products in numerous fields of application, for example as pharmaceuticals or as constituents of radiation-sensitive compositions.

Examples of pharmaceuticals having an activity against malaria are hexachloro-p-xylene

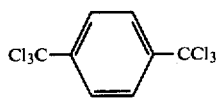

or 2-(trichloromethyl-phenyl)-5-trichloromethyl-1,3,4-oxadiazoles

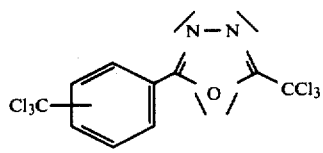

(see G. Ehrhart and H. Ruschig, "Arzneimittel (Medicaments)", published by Chemie-Weinheim, 1972, pages (197/198).

In radiation-sensitive compositions, the compounds carrying halogenomethyl groups can be used as photoinitiators, i.e., on the one hand, the free radicals formed from these compounds under the action of radiation can be utilized for initiating polymerization reactions, crosslinking reactions or changes in color, or, on the other hand, secondary reactions are effected by the acid liberated from these compounds. The photoinitiators which have been known for a long time include, for example, tetrabromomethane CBr$_4$, tribromo-acetophenone Br$_3$C-CO-C$_6$H$_5$ and iodoform CHI$_2$. These relatively easily accessible compounds, however, absorb only short-wave UV light so that, in the excitation range of the exposure lamps customary in reproduction technology, they have only a low spectral sensitivity and must therefore be excited with the aid of an additional sensitizer.

Attempts have been made to overcome the above-mentioned difficulties by the use of halogeno-organic compounds which contain certain chromophores. Among the state of the art, for example, the following printed publications are known:

German Auslegeschrift No. 1,949,010 discloses the use of halogeno-methylated benzophenones as initiators of the photopolymerization of unsaturated compounds, an example of such a photoinitiator being the following compound:

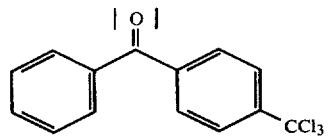

German Pat. No. 2,027,467, equivalent to U.S. Pat. No. 3,751,259, describes a photopolymerizable copying composition which contains an ethylenically unsaturated polymerizable compound, a binder and, as the photoinitiator, an optionally substituted compound from the acridine or phenazine series.

The s-triazine derivatives of German Offenlegungsschrift No. 2,243,621, contain at least one trihalogenomethyl group and at least one chromophoric grouping which forms a conjugated system with the triazine ring via ethylenically unsaturated groups; these are effective as photoinitiators in compositions which contain an ethylenically unsaturated compound which is capable of an addition polymerization initiated by free radicals. An example of such a photoinitiator is the following compound:

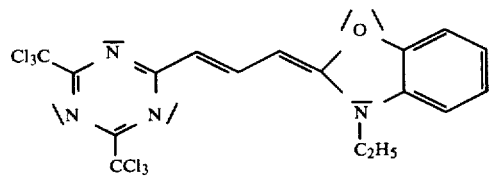

The mixture of substances according to German Auslegeschrift No. 2,306,248, equivalent to U.S. Pat. No. 3,779,778, which is rendered soluble by exposure, contains a water-insoluble compound (aryl alkyl acetals and aryl alkyl aminals) which becomes soluble under the action of a photolytically formed acid, and, as the photoinitiator, a stable halogen-containing organic compound which has a neutral reaction under normal conditions and which can be split photolytically and thereby gives an acid. Examples of suitable photoinitiators are: carbon tetrabromide, hexabromoethane, trichloroacetophenone, halogenomethyl-s-triazines or vinylhalogenomethyl-s-triazines (for the latter, see also German Offenlegungsschrift No. 2,243,621).

German Offenlegungsschrift No. 2,718,259, equivalent to U.S. Pat. No. 4,189,323, discloses a radiation-sensitive composition which, as the radiation-sensitive compound, contains an s-triazine derivative having at least one halogenomethyl group and one dinuclear or polynuclear aromatic radical as substituents; an example of such a radiation-sensitive compound is the following compound:

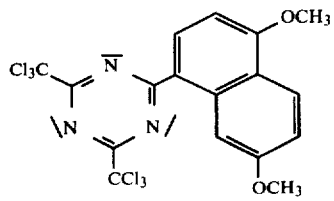

German Offenlegungsschrift No. 2,851,472, describes a light-sensitive composition which, as the photoinitiator, contains a 2-halogenomethyl-5-vinyl-1,3,4-oxadiazole derivative; an example of such a photoinitiator is the following compound:

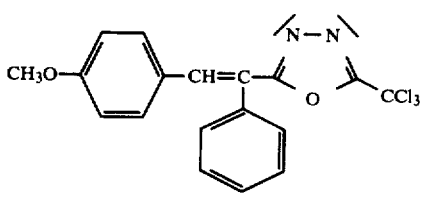

The photoinitiators of the UV-sensitive compositions according to U.S. Pat. No. 3,912,606, are benzoxazoles which carry halogenomethyl groups and in which this halogenomethyl group is bonded directly or via a benzene ring to the 2-position. An example of such a photoinitiator is the following compound:

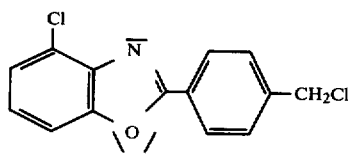

The photoinitiators or radiation-sensitive compounds known from the state of the art have, however, one or more of the following disadvantages:

the compounds which do not contain any halogen which can be split off photolytically, cannot be used for acid-catalyzed modifications to a molecule (for example, German Offenlegungsschrift No. 2,027,467), certain syntheses satisfactorily produce only monohalogenomethyl substituents in the molecule (for example U.S. Pat. No. 3,912,606), although the absorption maxima are shifted relative to the known simple photoinitiators, the absorption is, relatively, still at too short a wavelength (for example U.S. Pat. No. 3,912,606), the reaction conditions for the production of the compounds are relatively severe, so that the reaction yield is low and the formation of undesired by-products is facilitated (for example, German Offenlegungsschrift No. 2,243,621, 2,718,259, or 2,851,472), or the use of certain catalysts permits the presence of only a few defined functional groups in the molecule (for example, German Offenlegungsschrift No. 2,718,259).

It is therefore the object of the present invention to synthesize new compounds which, in particular, are radiation-sensitive and thus can be used preferably in the field of reproduction technology, in which further developments are rapidly taking place at present. The compounds should be relatively easily accessible and have wide scope for variations, so that they can be adapted in an optimum manner to the most diverse requirements in the particular field of application; for example, they should have a spectral sensitivity which, relative to the emission of conventional radiation sources, includes a wide absorption range, i.e., they should be sensitive in particular in the ultraviolet and shortwave visible range of light. Additionally, if the compounds are employed in radiation-sensitive compositions in the reproduction sector (for example on printing plates), they should be able to produce a clearly visible colored image of the original just after the exposure, so that it becomes possible, for example, to correct exposure errors even before the actual development of the radiation-sensitive composition.

This object is achieved, according to the invention, by 2-(halogenomethyl-phenyl)-4-halogeno-oxazole derivatives of the general formula I

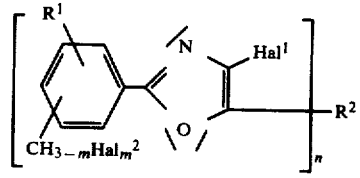

wherein $Hal^1$ is a halogen atom, $Hal^2$ is a chlorine or bromine atom, m is an integer from 1 to 3, n is an integer from 1 to 4, $R^1$ is a hydrogen atom or a further $CH_{3-m}Hal^2_m$ group and $R^2$ is an n-valent, optionally substituted, unsaturated organic radical.

In a preferred embodiment of the invention, in the general formula I, $Hal^1$ is a chlorine or bromine atom, $Hal^2$ is a chlorine atom, m is the number 3, n is the number 1 or 2, $R^1$ is a hydrogen atom or a further $CCl_3$ group and $R^2$ is a 1-valent or 2-valent, optionally substituted, at most tetranuclear aromatic or heteroaromatic radical which may be partially hydrogenated and, at an unsaturated ring carbon atom, is linked, directly or via a chain which contains up to 4 exclusively unsaturated carbon atoms, to the oxazolyl part of the molecule according to the general formula I.

Examples of the radical $R^2$ are the radicals: phenyl, naphthyl, indenyl, fluorenyl, anthracenyl, phenanthrenyl, pyrenyl, biphenyl, stilbenyl, styryl, furanyl benzofuranyl, dibenzofuranyl, pyrrolyl, indolyl carbazolyl, thienyl, benzothienyl, imidazolyl, benzimidazolyl, oxazolyl, benzoxazolyl, isoxazolyl, thiazolyl, benzothiazolyl, triazolyl, oxadiazolyl, thiadiazolyl, pyridyl, quinolyl, isoquinolyl, acridyl, pyrimidyl, benzopyranyl, benzothianyl and vinyl. Examples of substituents which the radical $R^2$ can carry (preferably up to four substituents) are, in addition to radicals such as have just been mentioned, by way of example for the radical $R^2$ itself, also the following radicals: alkyl, cycloalkyl, alkenyl, cycloalkenyl, alkylene, alkoxy, carboxy, carbalkoxy, carbalkoximino, carboxamido, cyano, carbonyl, sulfonyl, amino, mono- and di-alkylamino having up to 6 carbon atoms, fluorine, chlorine, bromine, iodine, nitro, trichloromethyl, trifluoromethyl and phenoxy.

Preferred substituents on the phenyl radical in the 2-position of the oxazole derivative are a trichloromethyl radical in the 4-position or 3-position of the phenyl ring.

It is known that 4-halogeno-2,5-diaryloxazoles can be prepared by passing a hydrogen halide at 0° C. into a solution of an aroyl cyanide and an aromatic aldehyde in ether and subsequently hydrolyzing the product (see M. Davis, R. Lakhan, and B. Ternai, J. Heterocycl. Chem. 14, 317, 1977).

The halogenomethyl-phenyl-substituted oxazole derivatives according to the invention can be prepared in an advantageous manner from a halogenomethyl-substituted benzaldehyde of the general formula II and a carboxylic acid cyanide of the general formula III, the following reaction equation symbolizing the course of the reaction (the symbols $Hal^1$, $Hal^2$, m, n, $R^1$ and $R^2$ have the meaning indicated above):

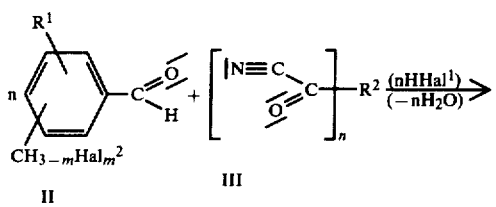

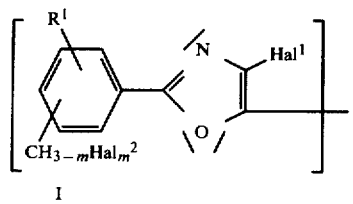

The halogenomethyl-substituted benzaldehydes, which are to be employed in this reaction which proceeds under mild conditions at temperatures between −30° C. and +20° C., preferably −20° C. to 0° C., in an inert organic solvent, such as, for example, tetrahydrofuran, diethyl ether, diisopropyl ether or diethylene glycol diethyl ether, which preferably solvates a hydrogen halide readily, are known only in the form of monohalogenomethyl derivatives (see, for example, J. W. Baker, J. A. L. Brieux and D. G. Saunders, J. Chem. Soc., 1956, 404 et seq.). The trichloromethyl-substituted benzaldehydes preferably used are novel and had to be made accessible first.

These new trichloromethyl-substituted benzaldehydes have the formula IV

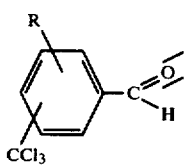

wherein R is H or CCl$_3$, and their derivatives V, which are stable and can readily be stored, have the formula

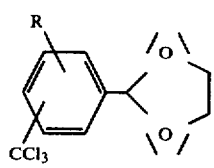

wherein R has the same meaning as in formula IV. They are prepared by reacting trichloromethyl-substituted 2-methoxyethyl benzoates with an oxonium salt to give dioxolanium salts which in turn are then further reacted with the complex hydride of an element of group III of the periodic table, to give the compounds V. The compounds IV are obtainable from the latter by the action of aqueous acids. A further preparation process for the compounds IV starts from trichloromethyl-substituted benzonitriles, from which IV is obtained by reaction with di-t-butyl-aluminum hydride and decomposition of the Al-organic complex compounds thus formed with aqueous mineral acid. Finally, the compounds IV are also obtained by reaction of trichloromethyl-substituted benzoyl halides with NaBH$_4$, with the addition of a metal halide of group II B or III B of the Periodic Table, such as, e.g., CuCl$_2$, CuCl, ZnCl$_2$, or CdCl$_2$ in an inert polar solvent, CdCl$_2$ being used preferably.

The carboxylic acid cyanides which are also required, as a further component, for the preparation of the compounds according to the invention, can be prepared by known processes (see, for example, Organic Synthesis Collective Volume III, 112–114, 1955), German Offenlegungsschriften Nos. 2,642,140, 2,708,182, and 2,708,183, Angew. Chem. 68, 425, 1956), for example by reaction of a carboxylic acid halide with a metal cyanide, such as NaCN, KCN, or CuCN.

As long as they do not carry any acid-sensitive grouping, almost any carboxylic acid cyanides can be employed as the second component, in addition to the benzaldehydes, for the preparation of the compounds according to the invention. Particularly suitable are carboxylic acid cyanides which extend the chromophore of the 2-phenyloxazole system, so that the resulting absorption of the compounds will be in the range from 250 to 500 nm, preferably 350 to 400 nm, and overlap the emission of the conventional exposure lamps. Aromatic, olefinic and heterocyclic-unsaturated carboxylic acid cyanides are therefore preferably used, and, for example, the following compounds are suitable:

Benzoyl cyanide, p-phenylbenzoyl cyanide, 3- and 4-bromobenzoyl cyanide, p-tert.-butylbenzoyl cyanide, o-, m- and p-chlorobenzoyl cyanide, 3,4- and 3,5-dichlorobenzoyl cyanide, 4-dimethylaminobenzoyl cyanide, p-cyanobenzoyl cyanide, 2,4- and 2,5-dimethoxybenzoyl cyanide, 3,4- and 3,5-dimethoxybenzoyl cyanide, 3,4,5-trimethoxybenzoyl cyanide, 3,4-methylenedioxybenzoyl cyanide, o-, m- and p-methoxybenzoyl cyanide, o-, m- and p-methylbenzoyl cyanide, 2,4-, 3,4- and 3,5-dimethylbenzoyl cyanide, 3,5-dinitrobenzoyl cyanide, m- and p-nitrobenzoyl cyanide, o-, m-and p-fluorobenzoyl cyanide, p-phenoxybenzoyl cyanide, m- and p-trichloromethylbenzoyl cyanide, 3,5-bis-(trichloromethyl)-benzoyl cyanide, naphthalene-1-carboxylic acid cyanide, naphthalene-2-carboxylic acid cyanide, 4-methylnaphthalene-1-carboxylic acid cyanide, 4-methoxynaphthalene-1-carboxylic acid cyanide, 6-methoxynaphthalene-2-carboxylic acid cyanide, 4-benzoxazolylbenzoyl cyanide, stilbene-4-carboxylic acid cyanide, 4'-methoxy-stilbene-4-carboxylic acid cyanide, 4'-cyano-stilbene-4-carboxylic acid cyanide, fluorene-2-carboxylic acid cyanide, terephthaloyl cyanide, isophthalic acid dicyanide, 2,6-pyridinedicarboxylic acid dicyanide, diphenyl ether 4,4'-dicarboxylic acid dicyanide, furancarboxylic acid cyanide, furan-2,5-dicarboxylic acid dicyanide, benzofurancarboxylic acid cyanide, cinnamoyl cyanide, 4-chlorocinnamoyl cyanide, 3,4-dimethoxycinnamoyl cyanide, o- and p-methoxycinnamoyl cyanide, 3,4-methylenedioxycinnamoyl cyanide, 3,4,5-trimethoxycinnamoyl cyanide, 4-nitrocinnamoyl cyanide and 4-methylcinnamoyl cyanide.

The molar ratios of the reactants can be varied within wide limits, and preferably the ratio used is within the range between 0.8 and 1.2 moles of one component per mole of the other component; an approximately 10% excess of carboxylic acid cyanide over the aldehyde employed is here particularly preferred.

The compounds according to the invention, prepared from the components which have been described in more detail above, include in particular the following, which have good radiation sensitivity:

2-(p-Trichloromethyl-phenyl)-4-chloro-oxazoles which carry the following substituents:

5-(p-Methoxyphenyl)-, 5-(p-chlorophenyl), 5-(4'-biphenylyl, 5-(p-benzoxazolylphenyl), 5-(4'-stilbenyl), 5-(2'-benzofuranyl), 5-(2'-naphthyl), 5-(6'-methoxy-2'-naphthyl) and 5-styryl.

Due to their radiation sensitivity, the new compounds have a wide spectrum of application. Thus, for example, they can be used as highly effective starters for photopolymerization reactions which can be initiated by free radicals. Suitable monomers which undergo corresponding polyadditions are, for example, mono-, bis-, tris- and tetra-acrylates and -methacrylates of monohydric or polyhydric alcohols or phenols, acrylic and methacrylic acid amides derived from mono- or polyfunctional amines, vinyl esters and vinylamides. Polymerizable compositions of this type can additionally contain varying quantities of fillers, binders, polymerization inhibitors, dyes, dye precursors, plasticizers, adhesion promoters or oxygen scavengers. If these compositions have been applied in the form of a layer to supports which may have been pretreated chemically, i.e., for example, to metal foils of steel, aluminum, chromium, copper or brass, films of plastic or paper, to glass, wood or ceramics or to composite materials comprising two or more of these substances, the light-sensitive layer also can be provided additionally with a covering layer which prevents access of oxygen.

The radiation-sensitive compounds are active as photoinitiators in concentrations as low as about 0.1% of the total solids in the composition, and an increase to more than 10% is in general disadvantageous. Preferably, concentrations from 1 to 5% are used.

Furthermore, the compounds according to the invention also can be employed in those radiation-sensitive compositions, in which a change of properties is initiated by acid catalysts which are formed during the photolysis of the initiator. In this connection, the cationic polymerization of systems which contain vinyl ethers, N-vinyl compounds, such as N-vinylcarbazole, or special acidlabile lactones may be mentioned; a participation of free-radical processes in some of these systems is not excluded. Aminoplasts, such as urea/formaldehyde resins, melamine/formaldehyde resins and other N-methylol compounds as well as phenol/formaldehyde resins are further compositions which can be cured by acids. Even though the curing of epoxy resins is in general effected by Lewis acids or by an acid of a type, in which the nucleophilic character of the anions is less pronounced than in the case of chloride and bromide, i.e. less pronounced than that of the anions of the hydrohalic acids formed during the photolysis of the new compounds, layers composed of epoxy resins and novolaks nevertheless readily cure in the presence of the compounds according to the invention.

A further advantageous property of the new compounds is their ability to cause color changes in colored systems during the photolysis; to induce the formation of color from color precursors, for example leuco compounds, or to effect bathochromic color shifts, and increases in the depth of color in mixtures which contain dye bases of the cyanine, merocyanine or styryl type. It is also possible, for example in the mixtures which are described in German Offenlegungsschrift No. 1,572,080 and which contain a dye base, N-vinylcarbazole and a halogenohydrocarbon, to replace the halogen compound tetrabromomethane by a quantity of compound according to the invention, which is only a fraction of that of the former. Color changes are also desired in industry, for example in the manufacture of printing forms, in order to be able to assess the result of copying after the exposure, but still before development.

The present compounds can be advantageously used in place of the acid donors mentioned in German Offenlegungsschriften Nos. 2,331,377 and 2,641,100.

A particularly preferred field of application of the compounds according to the invention are compositions which, in addition to these compounds, contain a compound, having at least one C—O—C grouping which can be split by acid, as an essential component. The following may be mentioned above all as compounds which can be split by acid:

(A) those having at least one orthocarboxylic acid ester grouping and/or carboxylic acid amide acetal grouping, it also being possible for the compounds to have a polymeric character and for the groupings to occur as linking elements in the main chain or as substituents in a side position, and (B) polymer compounds having recurring acetal and/or ketal groupings in which both the α-C atoms of the alcohols, required for building up these groupings, are aliphatic.

Compounds of the type A, which can be split by acid, as components of radiation-sensitive copying compositions are extensively described in German Offenlegungsschriften Nos. 2,610,842 or 2,928,636; copying compositions which contain compounds of the type B are the subject of German Auslegeschrift No. 2,718,254.

Examples of further compounds which can be split by acid are the special aryl alkyl acetals and aryl alkyl aminals of German Auslegeschrift No. 2,306,248, which are likewise degraded by the products of the photolysis of the compounds according to the invention.

Those compositions in which molecules, the presence of which has a substantial influence on the chemical and/or physical properties of the composition, are directly or indirectly converted into smaller molecules by the action of actinic radiation, have in general an increased solubility, tackiness or volatility in the irradiated areas. These portions can be removed by suitable measures, for example by dissolving them out with the aid of a developer fluid. In these cases, the copying compositions are called positive-working systems.

The novolak condensation resins, proven in many positive copying compositions, have also proved to be especially useful and advantageous as an additive when the compounds according to the invention are used in copying compositions together with compounds which can be split by acid. They promote the sharp differentiation between the exposed and unexposed parts of the layer on development, particularly in the case of the more highly condensed resins with substituted phenols as the condensation partner of formaldehyde. The nature and quantity of the novolak resins can vary depending on the particular application; novolak proportions in total solids between 30 and 90, particularly preferably 55–85, percent by weight are preferred.

Additionally, numerous other resins also can be co-used, preferably vinyl polymers, such as polyvinyl acetates, polyacrylates, polyvinyl ethers and polyvinylpyrrolidones, which can in turn have been modified by comonomers. The most advantageous proportion of these resins depends on the technological requirements and on the influence which they exert on the development conditions, and in general this is not more than 20 percent of the novolak. For special requirements, such as flexibility, adhesion, gloss, and the like, the light-sensitive composition additionally can contain small quantities of substances, such as polyglycols, cellulose derivatives, such as ethylcellulose, wetting agents, dyes and finely particulate pigments as well as UV absorbers, if required. Developing is preferably carried out with aqueous-alkaline developers usual in industry, which can also contain small proportions of organic solvents.

The supports already mentioned in connection with the photopolymerizable compositions also can be used for positive-working copying compositions, as well as the silicon and silicon dioxide surfaces usual in microelectronics.

The quantity of the compounds according to the invention employed as a photoinitiator can vary very widely in the positive-working copying compositions, depending on the substance and layer. Relatively good results are obtained with quantities between about 0.1 and 10 percent, relative to total solids, and about 1 to 5 percent are preferred. In the case of layers having thicknesses of more than 10 μm, it is advisable to use a relatively small quantity of acid donor.

In principle, electromagnetic radiation of wavelengths of up to about 600 nm is suitable for the initiation of reactions of the type described in the radiation-sensitive compositions containing the compound according to the invention. The preferred wavelength range extends from 250 to 500 nm.

The diversity of the compounds according to the invention, the absorption maxima of which in some cases still extend far into the visible part of the spectrum and the absorption range of which can extend beyond 500 nm, makes it possible to match the photoinitiator in an optimum manner to the light source used. However, sensitization is not excluded in principle. The following are examples of light sources:

Tubular lamps, pulsed xenon lamps, metal halide-doped high-pressure mercury vapor lamps and carbon arc lamps.

Furthermore, exposure in conventional projection and enlarging apparatuses under the light of metal filament lamps and contact exposure with ordinary incandescent lamps are possible in the case of the light-sensitive copying compositions according to the invention. The exposure also can be carried out with the coherent light of a laser. Short-wave lasers of appropriate power, for example argon lasers, krypton ion lasers, dyestuff lasers and helium/cadmium lasers, which emit especially between 250 and 500 nm, are suitable for the purposes of the present invention. The laser beam is controlled by means of a preset programmed line-scanning and/or screen-scanning motion.

Exposure with electron beams is a further possibility of differentiation. Electron beams can thoroughly decompose and cross-link copying compositions, which contain a compound according to the invention and a compound which can be split by acid, as well as many other organic materials, so that a negative image is formed when the unirradiated portions are removed by solvents or by exposure without an original, and development. If the intensity of the electron beam is relatively low and/or the scanning speed is relatively high, however, the electron beam effects a differentiation in the direction of higher solubility, i.e., the irradiated portions of the layer can be removed by the developer. The most advantageous conditions can be readily determined by preliminary experiments.

The preferred use of the radiation-sensitive compositions which contain a compound according to the invention is in the manufacture of printing forms, i.e. in particular offset forms, halftone gravure-printing and screen-printing forms, in copying lacquers and in so-called dry resists.

The examples which follow are intended to explain the invention in more detail and, initially, the preparation of various compounds according to the invention is described, and this is followed by the use of some of these compounds in radiation-sensitive compositions.

In the examples, parts by weight (p.b.w.) and parts by volume (p.b.v.) have the same relationship as that of the g and the ml. Percentage data and quantitative data are to be understood as weight units, unless otherwise stated.

TABLE I

Examples of compounds of the general formula VI

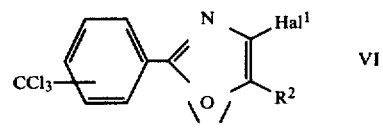

(i.e. of the formula 1 with $R^1$ = H, $Hal^2$ = Cl, m = 3, n = 1), the compounds 1 to 16 having the trichloromethyl group in the 4-position and compound 17 having the trichloromethyl group in the 3-position of the phenyl ring; among these, compound 16 differs in that the radical $R^2$ is divalent and n hence becomes 2.

| Compound No. | $R^2$ = | $Hal^1$ = | Melting point (°C.) | Long-wave absorption maximum in DMF $\lambda_{max}$ (lgε) [nm] |
|---|---|---|---|---|
| 1 | –⟨phenyl⟩ | Cl | 129–30 | 326 (4.40) |
| 2 | –⟨phenyl⟩ | Br | 123–25 | 325 (4.40) |
| 3 | –⟨phenyl⟩–CH₃ | Cl | 150–51 | 332 (4.41) |
| 4 | –⟨phenyl⟩–OCH₃ | Cl | 170–71 | 340 (4.40) |
| 5 | –⟨phenyl⟩–Cl | Cl | 154–55 | 326 (4.46) |
| 6 | –⟨phenyl⟩–⟨phenyl⟩ | Cl | 152 | 343 (4.56) |
| 7 | –⟨phenyl⟩–⟨benzoxazole⟩ | Cl | 259–60 | 359 (4.71) |
| 8 | –⟨phenyl⟩–CH=CH–⟨phenyl⟩ | Cl | 160–62 | 366 (4.71) |
| 9 | –⟨phenyl⟩–CCl₃ | Cl | 176–77 | 337 (4.52) |
| 10 | –⟨phenyl⟩–CCl₃ | Br | 169–70 | 337 (4.51) |

TABLE I-continued

Examples of compounds of the general formula VI

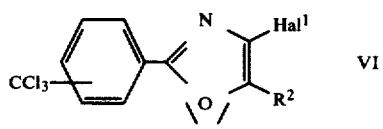

(i.e. of the formula I with $R^1$ = H, $Hal^2$ = Cl, m = 3, n = 1), the compounds 1 to 16 having the trichloromethyl group in the 4-position and compound 17 having the trichloromethyl group in the 3-position of the phenyl ring; among these, compound 16 differs in that the radical $R^2$ is divalent and n hence becomes 2.

| Compound No. | $R^2$ = | $Hal^1$ = | Melting point (°C.) | Long-wave absorption maximum in DMF $\lambda_{max}$ (lg$\epsilon$) [nm] |
|---|---|---|---|---|
| 11 | (1-naphthyl) | Cl | 121–22 | 323 (4.33) |
| 12 | (2-naphthyl) | Cl | 162–64 | 341 (4.49) |
| 13 | (6-methoxy-2-naphthyl) | Cl | 209–11 | 351 (4.48) |
| 14 | (benzofuranyl) | Cl | 176–79 | 349 (4.48) |
| 15 | (styryl) | Cl | 139–40 | 359 (4.50) |
| 16 | (4,4'-oxydiphenyl) | Cl | 222–24 | 342 (4.74) |
| 17 | (p-methoxyphenyl) | Cl | 161–62 | 330 (4.37) |

EXAMPLE 1 (COMPOUND 4)

A solution of 8 g of p-trichloromethylbenzaldehyde and 6.5 g of p-methoxybenzoyl cyanide in 40 ml of dry tetrahydrofuran is saturated at −20° C. to −30° C. with hydrogen chloride gas. After 15 hours at 0° C., the mixture is poured onto ice. The precipitated product is filtered off with suction and recrystallized from acetone.

Yield 11.2 g (77% of theoretical)

| $C_{17}H_{11}Cl_4NO_2$ calculated: | C 50.66 H 2.75 N 3.47 Cl 35.18 |
|---|---|
| (403.09) found: | C 50.7 H 2.7 N 3.5 Cl 35.1 |
| Melting point: | 170–171° C. |
| $^1$H-NMR spectrum (CDCl$_3$): | $\delta$ = 3.85 (s, OCH$_3$), 7.0 (d, J = 9 Hz, 2 H), 7.85 (d, J = 9 Hz, 2 H), 8.05 (s, 4 H) |
| UV spectrum (DMF): | $\lambda_{max}$ ($\epsilon$) = 340 nm (25,100) |

EXAMPLE 2 (COMPOUND 5)

11.5 g of a mixture composed of p-trichloromethylbenzaldehyde to the extent of 70 percent and p-trichloromethylbenzonitrile to the extent of 30 percent, and 6.5 g of p-chlorobenzoyl cyanide are reacted in 40 ml of dry tetrahydrofuran, in accordance with the procedure of Example 1. After recrystallization from acetone, 11.6 g (70% of theoretical) of compound 5 are obtained.

| $C_{16}H_8Cl_5NO$ calculated: | C 47.16 H 1.98 N 3.44 Cl 43.50 |
|---|---|
| (407.51) found: | C 47.2 H 2.0 N 3.5 Cl 43.2 |
| Melting point: | 154–155° C. |
| $^1$H-NMR spectrum (CDCl$_3$): | $\delta$ = 7.4 (d, J = 9 Hz, 2 H), 7.85 (d, J = 9 Hz, 2 H), 8.05 (s, 4 H) |
| UV spectrum (DMF): | $\lambda_{max}$ ($\epsilon$) = 326 (28,800), 332 nm (S, 28,600) |

EXAMPLE 3 (COMPOUND 6)

8 g of trichloromethylbenzaldehyde and 8.3 g of p-phenylbenzoyl cyanide are reacted in accordance with the procedure of Example 1.

Yield 11.1 g (67% of theoretical)

| $C_{22}H_{13}Cl_4NO$ calculated: | C 58.83 H 2.92 N 3.12 Cl 31.57 |
|---|---|
| (449.16) found: | C 58.7 H 3.2 N 3.1 Cl 31.5 |
| Melting point: | 152° C. |
| $^1$H-NMR spectrum (CDCl$_3$): | $\delta$ = 7.3–7.7 (m, 5 H), 7.7 (d, J = 9 Hz, 2 H), 8.0 (d, J = 9 Hz, 2 H), 8.05 (s, 4 H) |
| UV spectrum (DMF): | $\lambda_{max}$ ($\epsilon$) = 277 (17,700), 343 nm (36,000) |

EXAMPLE 4 (COMPOUND 10)

8 g of p-trichloromethylbenzaldehyde and 9.5 g of p-trichloromethylbenzoyl cyanide in 40 ml of diethyl ether are saturated at −20° C. with hydrogen bromide gas. After 15 hours at 0° C., the mixture is poured onto ice and the precipitated product is recrystallized from acetone.

Yield 10.1 g (52% of theoretical)

| $C_{17}H_8BrCl_6NO$ calculated: | C 38.17 H 1.51 N 2.62 Cl 39.77 |
|---|---|
| (534.88) found: | C 38.4 H 1.8 N 2.6 Cl 39.2 |
| Melting point: | 169–170° C. |
| $^1$H-NMR spectrum (CDCl$_3$): | $\delta$ = 8.0 (s, 4 H), 8.05 (s, 4 H) |
| UV spectrum (DMF): | $\lambda_{max}$ ($\epsilon$) = 328 (32,200), 337 nm (32,200) |

EXAMPLE 5 (COMPOUND 15)

4.2 g of cinnamoyl cyanide are reacted in accordance with the procedure of Example 1.

| $C_{18}H_{11}Cl_4NO$ calculated: | C 54.17 H 2.78 N 3.51 Cl 35.53 |
|---|---|
| (399.10) found: | C 54.3 H 2.8 N 3.5 Cl 34.4 |
| Melting point: | 139–140° C. |
| $^1$H-NMR spectrum (CDCl$_3$): | $\delta$ = 6.85 (d, J = 16 Hz, olefinic H), 7.2 (d, J = 16 Hz, olefinic H), 7.4 (m, 5 H), 8.05 (s, 4 H) |
| UV spectrum (DMF): | $\lambda_{max}$ ($\epsilon$) = 359 nm (31,800) |

EXAMPLE 6 (COMPOUND 16)

15 g of a mixture composed of p-trichloromethylbenzaldehyde to the extent of 70 percent and of p-trichloromethylbenzonitrile to the extent of 30 percent, and 5.8 g of 4,4'-bis-(cyanocarbonyl)-diphenyl ether are reacted in accordance with the procedure of Example 2. After recrystallization from ethyl acetate, 6.3 g (41% of theoretical) of compound 16 are obtained.

| $C_{32}H_{16}Cl_8N_2O_3$ calculated: | C 50.56 H 2.12 N 3.69 Cl 37.31 |
|---|---|
| (760.12) found: | C 51.0 H 2.2 N 3.6 Cl 37.0 |
| Melting point: | 222–224° C. |
| $^1$H-NMR spectrum (CDCl$_3$): | $\delta =$ 7.15 (d, J = 9 Hz, 4 H), 7.95 (d, J = 9 Hz, 4 H), 8.05 (s, 8 H) |
| UV spectrum (DMF): | $\lambda_{max}$ ($\epsilon$) = 342 nm (55,000) |

EXAMPLE 7 (COMPOUND 17)

8 g of trichloromethylbenzaldehyde are reacted in accordance with the procedure of Example 1. Yield 12.3 g (85% of theoretical)

| $C_{17}H_{11}Cl_4NO_2$ calculated: | C 50.66 H 2.75 N 3.47 Cl 35.18 |
|---|---|
| (403.09) found: | C 50.4 H 2.9 N 3.5 Cl 35.2 |
| Melting point: | 161–162° C. |
| $^1$H-NMR spectrum (CDCl$_3$): | $\delta =$ 3.85 (s, OCH$_3$), 7.0 (d, J = 9 Hz, 2 H), 7.5 (t, J = 8 Hz, H), 7.85 (d, J = 9 Hz, 2 H), 8.05 (m, 2 H), 8.6 (broad s, H) |
| UV spectrum (DMF): | $\lambda_{max}$ ($\epsilon$) = 330 nm (23,300) |

EXAMPLE 8

An electrochemically roughened aluminum plate is coated with a solution composed of:

6.5 parts by weight of trimethylolethane triacrylate
6.5 parts by weight of a methacrylic acid/methyl methacrylate copolymer (acid number 115)
0.2 part by weight of compound (photoinitiator) 1
64.0 parts by weight of ethylene glycol monoethyl ether
22.6 parts by weight of butyl acetate, and
0.2 part by weight of 2,4-dinitro-6-chloro-2'-acetamido-5'-methoxy-4'-($\beta$-hydroxyethyl-$\beta$'-cyanoethyl)-amino-azobenzene in such a way that, after drying, a layer weight of about 3 to 4 g/m$^2$ is obtained. This coated plate is additionally provided with a polyvinyl alcohol top coat of 4 $\mu$m thickness and is contact-exposed from a distance of about 10 cm in a vacuum exposure frame with TLAK 20W/05 tubular lamps from Messrs. Philips. The negative image of the original is developed with a 1.5% concentration aqueous sodium metasilicate solution.

In Table II, the number of cured steps of a step wedge is listed, the photoinitiator 1 being replaced by an equimolar amount of another photoinitiator. A difference of two wedge steps here corresponds to twice the light sensitivity of the light-sensitive layer.

TABLE II

| Compound No. | Cured wedge steps according to Example 1 (t = exposure time) | |
|---|---|---|
| | t = 45 seconds | t = 2 minutes |
| 1 | 6 | 10 |
| 2 | 5 | 9 |
| 3 | 7 | 9 |
| 4 | 7 | 10 |
| 5 | 7 | 10 |
| 6 | 7 | 10 |
| 7 | 4 | 7 |
| 8 | 9 | 11 |
| 9 | 6 | 9 |
| 10 | 5 | 9 |
| 11 | 4 | 7 |
| 12 | 7 | 9 |
| 13 | 8 | 11 |
| 14 | 8 | 10 |
| 15 | 8 | 10 |
| 16 | 5 | 9 |
| 17 | 4 | 7 |
| Bis-(trichloromethyl)-(4-methoxystyryl)-s-triazine according to German Offenlegungsschrift No. 2,243,621 | 5 | 8 |
| 9-Phenylacridine according to German Patent No. 2,027,467 | 10 | 13 |

The activity of a large number of products according to the invention is superior to that of the compound according to German Offenlegungsschrift No. 2,243,621, which is used in practice and likewise contains a trihalogenomethyl group. The compound according to German Offenlegungsschrift No. 2,027,467, which is also used in practice and does not contain any trihalogenomethyl group, is admittedly somewhat more active in the present light-sensitive composition than the examples, listed here, of the compounds according to the invention, but it can be employed only in radiation-sensitive compositions which contain photopolymerizable monomers, because there is no halogen which can be split off photolytically, i.e., a use in radiation-sensitive compositions which contain a compound, the solubility of which is modified by the action of an acid, is then not possible—in contrast to the compounds according to the invention.

EXAMPLE 9

Using 0.2 part by weight of the light-sensitive compound 1, a layer composition according to Example 8 is subjected, before exposure, to a storage test at 100° C. As Table III shows, a loss of activity cannot be detected.

TABLE III

| Storage period (minutes) at 100° C. before exposure | Cured wedge steps when using the initiator 1 - (t = 2 minutes) |
|---|---|
| 0 | 9 |
| 60 | 8 |
| 90 | 8 |
| 120 | 7 |
| 150 | 7 |
| 180 | 7 |
| 210 | 7 |
| 240 | 8 |

EXAMPLE 10

An electrochemically roughened aluminum plate is coated with a solution composed of
6.5 parts by weight of trimethylolethane triacrylate 6.5 parts by weight of a methacrylic acid/methyl methacrylate copolymer (acid number 115)
0.2 part by weight of photoinitiator 4
64.0 parts by weight of ethylene glycol monoethyl ether
22.6 parts by weight of butyl acetate, and
0.24 part by weight of leucomalachite green
and provided with a polyvinyl alcohol top coat. After an exposure time of 60 seconds according to Example 8, a negative, green image of the original is obtained which, by development, is fixed to give a printable plate. If leucomalachite green is replaced by cresol red, a red image of the original is obtained.

EXAMPLE 11

A brushed aluminum sheet is coated by the dipping process with a solution composed of
10 parts by volume of methyl ethyl ketone
1 part by weight of a cresol/formaldehyde novolak
0.3 part by weight of a polycondensation product of triethylene glycol and ethylbutyraldehyde, and
0.015 part by weight of one of the compounds according to the invention
and exposed in accordance with Example 8, and the positive image of the original is developed with a solution containing
5.5 parts by weight of sodium metasilicate.9H$_2$O
3.4 parts by weight of trisodium phosphate.12H$_2$O
0.4 part by weight of sodium dihydrogen phosphate and
90.7 parts by weight of desalinated water.

The number of wedge steps which can be developed is indicated in Table IV.

TABLE IV

| Compound No. | Wedge steps (t = 2 minutes) | Compound No. | Wedge steps (t = 2 minutes) |
|---|---|---|---|
| 1 | 7 | 12 | 10 |
| 2 | 6 | 13 | 11 |
| 3 | 8 | 14 | 10 |
| 4 | 11 | 15 | 11 |
| 5 | 7 | 16 | 10 |
| 6 | 8 | 17 | 5 |
| 7 | 8 | Bis-(trichloromethyl)-(4-methoxystyryl)-s-triazine according to German Offenlegungsschrift No. 2,243,621 | 9 |
| 8 | 11 | | |
| 9 | 7 | | |
| 10 | 6 | | |
| 11 | 7 | | |

The activity of the compound according to German Offenlegungsschrift No. 2,243,621, which is used in practice, is exceeded by many of the compounds according to the invention.

EXAMPLE 12

5 mg of methyl red or cresol red are admixed to a layer giving a positive image, according to Example 11. After exposure, a red-colored image of the original is obtained.

EXAMPLE 13

In accordance with Example 8, a layer is prepared using the photoinitiator 12 and is subjected to exposure for different lengths of time. The number of wedge steps cured in each case rises linearly with the duration of exposure (Table V).

TABLE V

| Duration of exposure (seconds) | Cured wedge steps |
|---|---|
| 10 | 1 |
| 20 | 3 |
| 40 | 6 |
| 80 | 8 |
| 160 | 10 |
| 320 | 12 |

It will be obvious to those skilled in the art that many modifications may be made within the scope of the present invention without departing from the spirit thereof, and the invention includes all such modifications.

What I claim is:

1. 2-(halogenomethyl-phenyl)-4-halogeno-oxazole derivatives of the general formula I

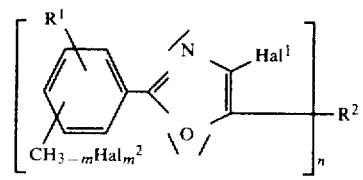

wherein
Hal$^1$ is a halogen atom,
Hal$^2$ is a chlorine or bromine atom,
m is an integer from 1 to 3,
n is an integer from 1 to 4,
R$^1$ is a hydrogen atom or a further CH$_{3-m}$Hal$^2_m$ group, and
R$^2$ is an n-valent, unsaturated organic radical.

2. Compounds of the general formula I, as claimed in claim 1, wherein:
Hal$^1$ is a chlorine or bromine atom,
Hal$^2$ is a chlorine atom,
m is the number 3,
n is the number 1 or 2,
R$^1$ is a hydrogen atom or a further CCl$_3$ group, and
R$^2$ is a 1-valent or 2-valent, at most tetranuclear aromatic or heteroaromatic radical which may be partially hydrogenated, and at an unsaturated ring carbon atom, is linked, directly or via a chain which contains up to four exclusively unsaturated carbon atoms, to the oxazolyl part of the molecule according to the general formula 1.

3. Compounds of the general formula I, as claimed in claim 2, wherein:
Hal$^1$ is a chlorine atom
n is the number 1,
R$^1$ is a hydrogen atom, and
R$^2$ is a substituted or unsubstituted phenyl or naphthyl radical.

4. Compounds of the general formula I, as claimed in claim 3, wherein the trichloromethyl group is in the 4-position of the phenyl group and R$^2$ is one of the group: methoxyphenyl, p-chlorophenyl, 4-biphenylyl, p-benzoxazolyl-phenyl, 4-stilbenyl, 2-benzofuranyl, 2-naphthyl, 6-methoxy-2-naphthyl, and styryl.

5. A radiation-sensitive composition which, as the radiation-sensitive compound, contains a 2-(halogenomethylphenyl)-4-halogeno-oxazole derivative of the general formula I, as claimed in any of claims 1 or 2 or 3.

6. A radiation-sensitive composition as claimed in claim 1 which additionally comprises an ethylenically unsaturated compound which is capable of undergoing a polymerization reaction initiated by free radicals.

7. A radiation-sensitive composition as claimed in claim 4, which additionally comprises a compound, the solubility of which is modified by the action of an acid.

8. A radiation-sensitive composition as claimed in claim 4, which additionally comprises a compound which is caused by acid catalysts to undergo a cationic polymerization.

9. A radiation-sensitive composition as claimed in claim 6, which comprises a compound which has at least one C-O-C grouping which can be split by acid, and the solubility of which is increased by the action of acids.

10. A radiation-sensitive composition as claimed in claim 4, wherein the radiation-sensitive compound of the formula I is contained in a quality of between 0.1 and 10 percent by weight.

11. A process for the preparation of the compounds as claimed in any of claims 1 or 2 or 3, which comprises reacting a halogenomethyl-benzaldehyde of the general formula II with a carboxylic acid cyanide of the general formula III

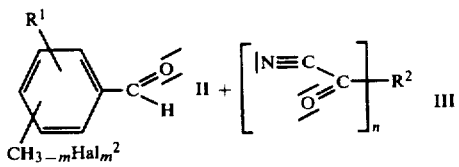

under the action of $HHal^1$ and liberating the reaction product by hydrolysis, the symbols $Hal^1$, $Hal^2$, m, n, $R^1$ and $R^2$ having the meaning indicated in any of claims 1 or 2 or 3.

* * * * *